United States Patent [19]
Dysarz

[11] Patent Number: 5,125,414
[45] Date of Patent: Jun. 30, 1992

[54] TRAP IN BARREL ONE HANDED RETRACTED BLOOD SAMPLING DEVICE

[76] Inventor: Edward D. Dysarz, 11423 Triola La., Houston, Tex. 77072

[21] Appl. No.: 569,088

[22] Filed: Aug. 17, 1990

Related U.S. Application Data

[63] Continuation-in-part of Ser. No. 466,722, Jan. 16, 1990.

[51] Int. Cl.$^5$ .............................................. A61B 5/00
[52] U.S. Cl. ............................................ 128/763; 604/195
[58] Field of Search ............... 604/195, 263, 158, 159, 604/162, 163, 164, 198, 110, 187; 128/763, 764, 765

[56] References Cited

U.S. PATENT DOCUMENTS

| | | | |
|---|---|---|---|
| 4,747,831 | 5/1988 | Kulli | 604/198 X |
| 4,813,940 | 3/1989 | Parry | 604/263 X |
| 4,834,718 | 5/1989 | McDonald | 604/163 X |

Primary Examiner—John D. Yasko

[57] ABSTRACT

A disposable blood sampling device having a needle cannula fixed to a slidable piston. The slidable piston assembly is held within the elongated hollow barrel of said blood sampling device by a compressed spring and a latch means. When said latch means is disengaged with said slidable piston and said needle cannula and said slidable piston is thrust into said elongated hollow barrel of said blood sampling device and holds said needle cannula fixed to said slidable piston within said elongated hollow barrel and is further prevented from being pushed out of said elongated hollow barrel by a rim in said elongated hollow barrel thus preventing any accidental injection of bacteria, virus or other undesirable material into others. The disengagement of said latch means with said piston assembly is accomplished with only one and the same hand that is used to inject the needle cannula into a body or into a vein inside of said body.

6 Claims, 4 Drawing Sheets

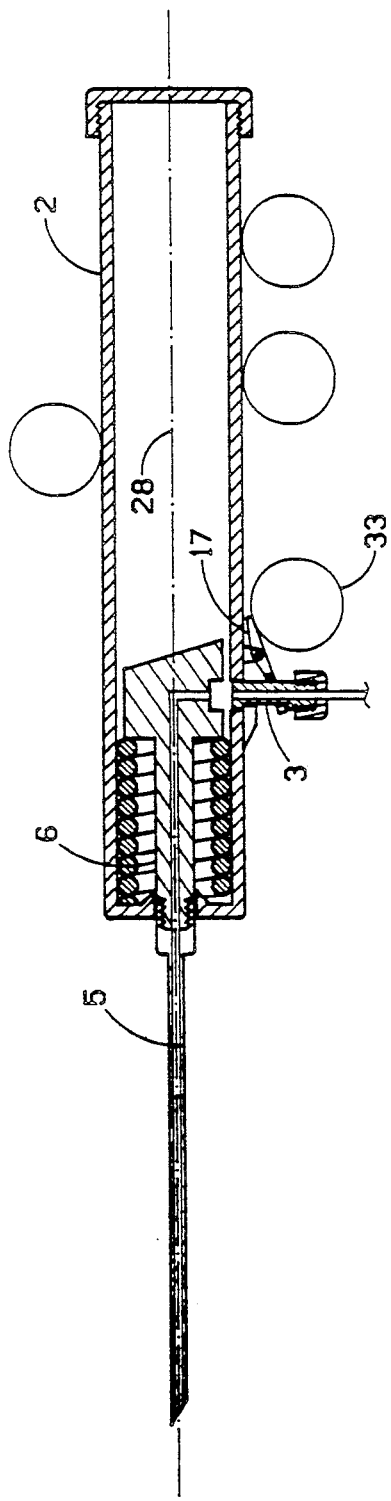
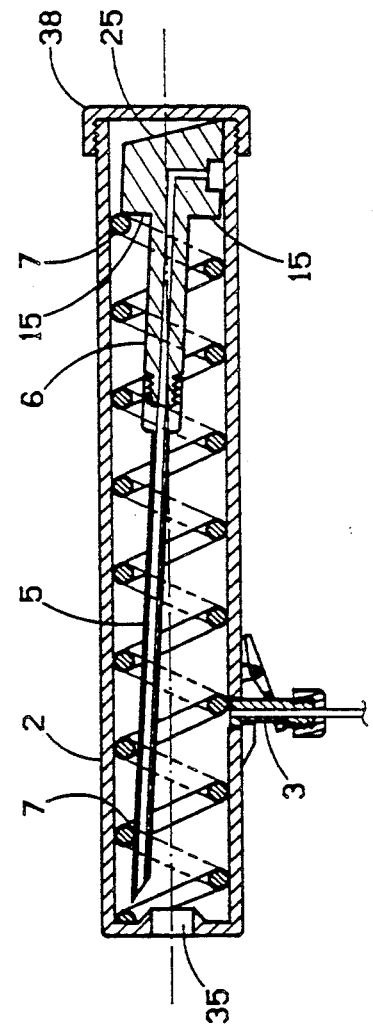
FIGURE 2
FIGURE 3

TRAP IN BARREL ONE HANDED RETRACTED BLOOD SAMPLING DEVICE

BACKGROUND OF THE INVENTION

There are several types of safety blood sampling designs available today. One such design is shown in a patent issued to JAGGER et al on JUN. 3, 1986 U.S. Pat. No. 4,592,744. This is a safety blood sampling device however it requires two (2) hands to operate or to cover up the needle cannula.

Blood samples are also taken with syringes and there are also many safety syringes available. Some of these designs have a sleeve or sheath that will cover the needle after it has been used. Some typical designs with sleeves or sheaths are Z. M. ROEHR et all U.S. Pat. No. 3,008,570, Z. M. ROEHR U.S. Pat. No. 3,107,785, BARTNER, et al U.S. Pat. No. 3,895,633, G K BURKE U.S. Pat. No. 3,306,291, GYURE et al U.S. Pat. No. 4,300,678, WINSTEAD HALL U.S. Pat. No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654, BRAGINETZ U.S. Pat. No. 466,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Still other designs have methods of bending the needle to render it harmless after the medication has been injected. Most of these designs have one major purpose and that is to prevent the spread of infectious diseases such as aids, hepatitis, or other diseases from an accidental injection with a contaminated needle into others after the needle of the syringe was inserted into a patient with the above mentioned disease. These various designs all work well to a degree, but they all fall short of their intended purpose during the act of covering the needle, or removing the needle, which requires two hands.

All of these designs require at least two hands to operate. The use of two hands to cover the contaminated needle is most unsatisfactory in that during the act of placing a second hand on the blood sampling device or syringe, the person holding the blood sampling device or syringe in one hand may be bumped and accidentally inject the needle into their other hand before it can grasp the syringe. Other accidental jabbing or injections can happen in an ambulance where just as a person tries to grasp the contaminated blood sampling device or syringe, the ambulance can hit a bump in the road causing the person holding the blood sampling device or syringe to accidentally stick another person or themselves with the contaminated needle. The need has developed for a blood sampling device or syringe that will cover the contaminated needle with the use of only one hand.

SUMMARY

It is the object of this invention to provide a blood sampling device wherein the needle of the blood sampling device is retracted into the barrel of the blood sampling device and protects others from an accidental pricking after it has been used; the needle cannula can be retracted into the barrel with the use of only one hand and that one hand being the hand that was used to inject the needle cannula into a patient.

Another object of the present invention is to render the blood sampling device useless after the needle cannula is retracted into the barrel of the blood sampling device to prevent the accidental reuse of the contaminated blood sampling device or to further prevent the reuse and abuse by users of illicit drugs.

It is still another object of the present invention to further prevent the accidental release of the needle cannula after the needle cannula is in the barrel of the blood sampling device.

The foregoing and other objects and advantages are attained by a blood sampling device, an elongated hollow barrel, a needle cannula, spring, slidable piston, and barrel flange in combination with a latching means wherein when said blood sampling device is used to inject a needle cannula into a vein in the body or part of the body in order to withdraw blood for testing purposes, the latch means is released and the spring further pushes the needle cannula fixed to the slidable piston into the elongated hollow barrel of the blood sampling device rendering the contaminated needle harmless to prevent the accidental pricking of others and to prevent a contaminated needle from being released from the barrel of the blood sampling device.

The features of the present invention can be best understood together with further objects and advantages by reference to the following descriptions taken in connection with accompanying drawing, wherein like numerals indicate like parts.

BRIEF DESCRIPTION OF THE DRAWINGS

FIG. 2 is a section elevation view of the preferred embodiment showing the latch means being withdrawn from the piston.

FIG. 3 is a section elevation view of the preferred embodiment showing the piston assembly with the needle pushed into the elongated hollow barrel of the blood sampling device by the spring.

FIG. 7 is a section elevation showing the piston with the needle cannula being disposed of.

DETAILED DESCRIPTION OF THE PREFERRED EMBODIMENTS

Figure 1:
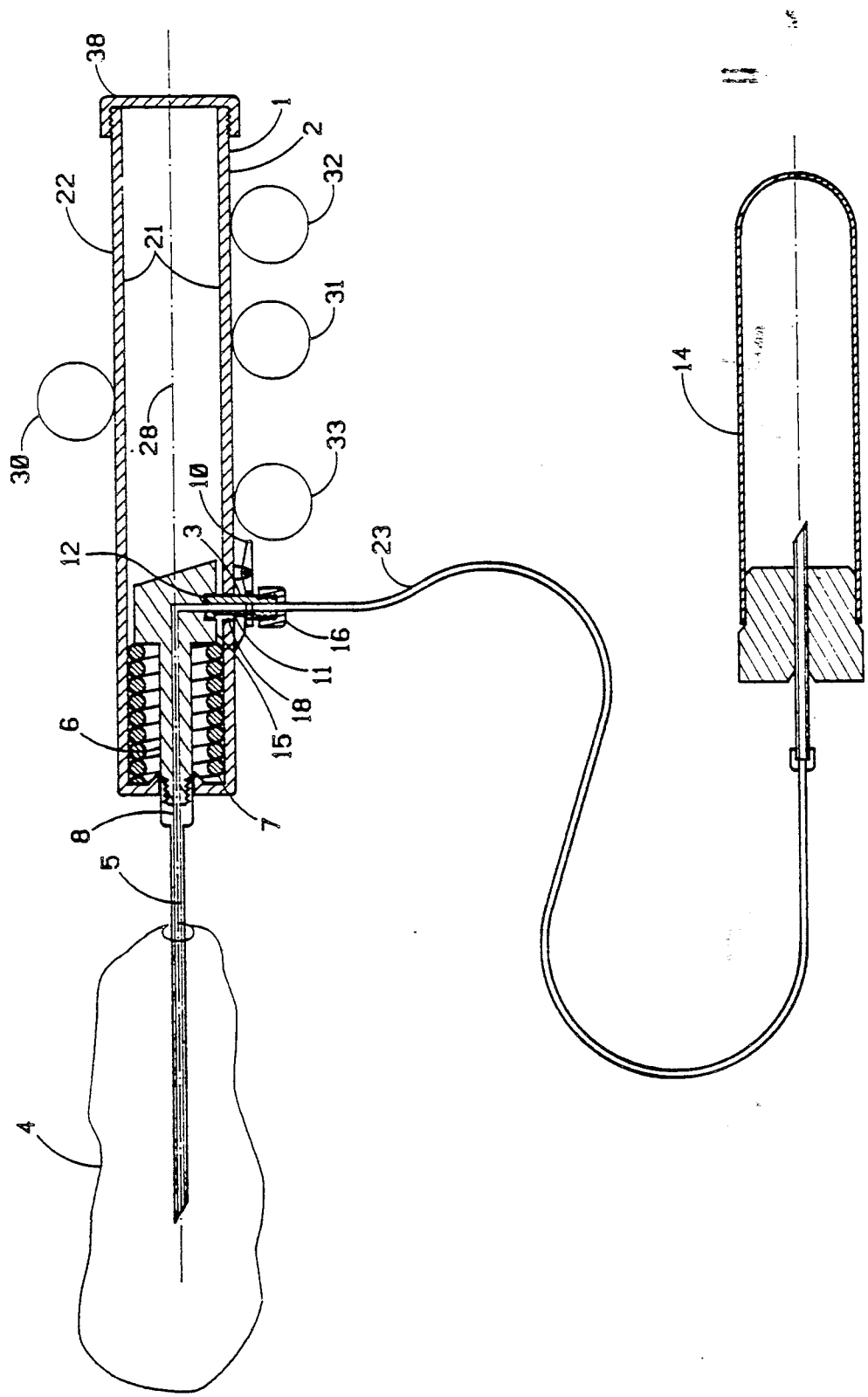
FIG. 1 is a section elevation view of the preferred embodiment of the present invention.

Referring to FIG. 1 there is shown a section elevation view of the blood sampling device 1 of the preferred embodiment.

The blood sampling device 1 is comprised of an elongated hollow barrel 2 which is a round tube like in configuration with a first end and a second end and with an inner surface 21 and an outer surface 22. The barrel flange 26 is shown at the first end of the elongated hollow barrel 2; the cap 38 is shown at the second end of the elongated hollow barrel 2. The barrel flange 26 retains the spring 7 within the elongated hollow barrel 2. The elongated hollow barrel 2 has a longitudinal axis 28 in the center of the elongated hollow barrel 2. The longitudinal axis 28 has a first end at the first end of the elongated hollow barrel 2 and a second end and runs the entire length of the elongated hollow barrel 2.

Also shown inside of the elongated hollow barrel 2 is the slidable piston 6 with a first end fixed to the second end of the needle cannula. The second end of the slidable piston 6 slopes and is not perpendicular to the longitudinal axis 28. The slidable piston 6 is shown held in place within the elongated hollow barrel 2 by the latch means 10 and the inner surface 21 of the elongated hollow barrel. The slidable piston 6 is further held in place at the first end by a compressed spring 7. The compressed spring 7 has a first end resting on the barrel flange 26 and a second end integral with the piston flange, 15. The compressed spring 7 is pushing on the piston flange 15 of the slidable piston 6. The slidable piston 6 is held and restrained in place by the latch means 10 on one side of the elongated hollow barrel 2. The latch 3 which is part of the latch means is shown inserted into the piston notch 12 that is formed in the slidable piston 6, engaging the slidable piston 6. The latch 3, further extends from the slidable piston 6, and through the latch hole 18 formed in the side of the elongated hollow barrel 2. The latch 3 is held in the piston notch 12 by friction or other suitable means.

The slidable piston 6 is further shown with a tunnel 8 or cannula formed inside of the slidable piston 6 and extending from the needle cannula 5 and into the latch means 10. The tunnel 8 further extends through the latch 3 of the latch means 10 where it is shown fixed to a tube 23 that is further connected to a vial 14 that will collect the blood sample. The tube 23 is further shown held to the latch 3 by a latch cap 16.

The blood sampling device 1 is shown held between fingers 31, 32, and 33. Finger 33 is near the latch means 10, and the thumb 30 when the needle cannula 5 is injected into the body 4 or vein not shown. The blood flows through the needle cannula and into the tunnel 8 through the latch 3 and through the tube 23 and into the vial 14 where it is collected. The blood may flow under its own pressure or the vial 14 may have a vacuum in to draw the blood.

Referring to FIG. 2, there is shown the needle cannula 5 withdrawn from the body and the finger 33 has moved over and onto the latch lever 17 to press in a direction of the longitudinal axis 28 causing the other end of the latch lever 17 to move away from the longitudinal axis 28 thus pulling up on the latch 3 that is restraining the slidable piston 6 within the elongated hollow barrel 2.

Referring to FIG. 3, there is shown a section elevation of the elongated hollow barrel 2 of the blood sampling device after the latch 3 has been disengaged or withdrawn from the slidable piston 6.

The spring 7 has thrust or pushes on the piston flange 15 causing the slidable piston 6 and the needle cannula 5 to move into the elongated hollow barrel 2 further causing the slope 25 of the slidable piston 6 and the needle cannula 5 to slope within the elongated hollow barrel 2. This slope of the slidable piston 6 and the needle cannula 5 will prevent the needle cannula 5 from reentering the needle cannula tunnel 35 thus rendering the needle cannula 5 safe from the accidental pricking of a person. The constant pressure of the spring 7 will also prevent the needle cannula 5 from entering the needle cannula tunnel 35.

Figure 4:
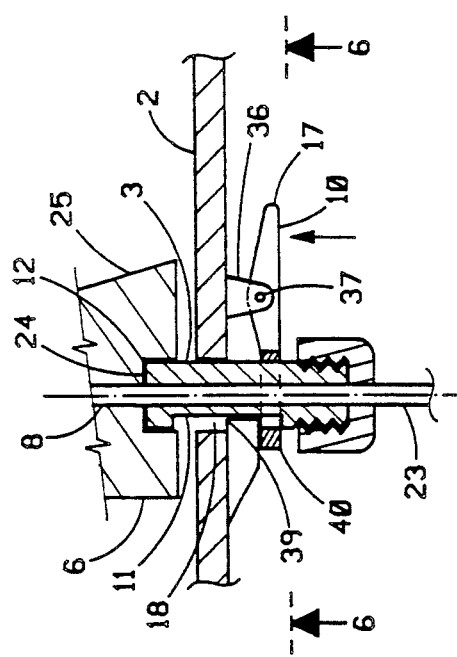
FIG. 4 is an enlarged section view of the latch means.

Referring to FIG. 4, there is shown an enlarged section elevation of the latch means 10. The latch 3 is shown plugged into piston notch 12 of the slidable piston 6 and is held in place by friction or a suitable adhesive. The slope 25 of the slidable piston 6 is also seen in FIG. 4. A gasket 24 is shown between the slidable piston 6 and the latch 3 forming a fluid tight connection for the tunnel 8 and the tube 23. A latch notch 11 is shown formed into one side of the latch 3 to be stopped by the latch stop 39 when the latch 3 is pulled out of the piston notch 12.

The latch 3 extends from the piston notch 12 and through the latch hole 18 formed in the elongated hollow barrel 2. The lever ring 40 is shown around the latch 3. The lever ring 40 is part of the latch lever 17. The latch lever 17 is supported on the elongated hollow barrel 2 by two latch fulcrums 36 and a latch pin 37 that extends through the latch fulcrums 36 and the latch lever 17.

Figure 5:
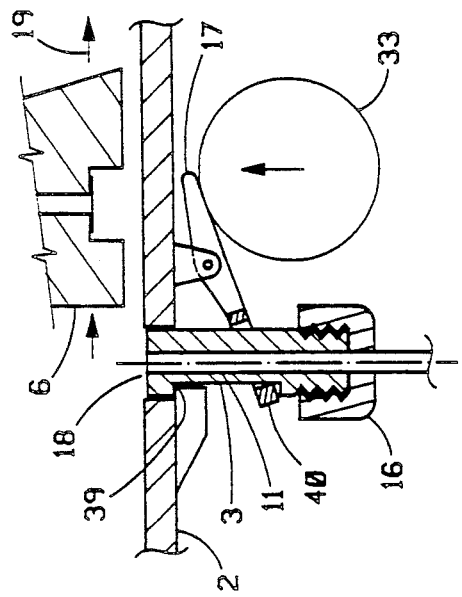
FIG. 5 is an enlarged section view of the latch means releasing the slidable piston.

Referring to FIG. 5, there is shown the latch lever 17 depressed by finger 33 causing the lever ring 40 to push on the latch cap 16 and thus to pull the latch 3 out of the slidable piston 6 which will allow the spring to push the slidable piston 6 in a capward direction 19. The latch 3 is prevented from moving out of the latch hole 18 formed in the elongated hollow barrel 2 by the latch stop 39 that is fixed to the elongated hollow barrel 2 and extends into the latch notch 11.

Figure 6:
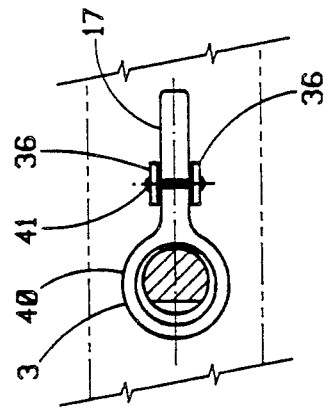
FIG. 6 is a plan view of of the latch ring and latch means.

Referring to FIG. 6, there is shown a section plan of the latch lever 17 and lever ring 40. The latch lever 17 is held to the latch fulcrums 36 by the latch pin 41 that extends from the first latch fulcrum 36. The lever ring 40 is shown around the latch 3.

Figure 7:
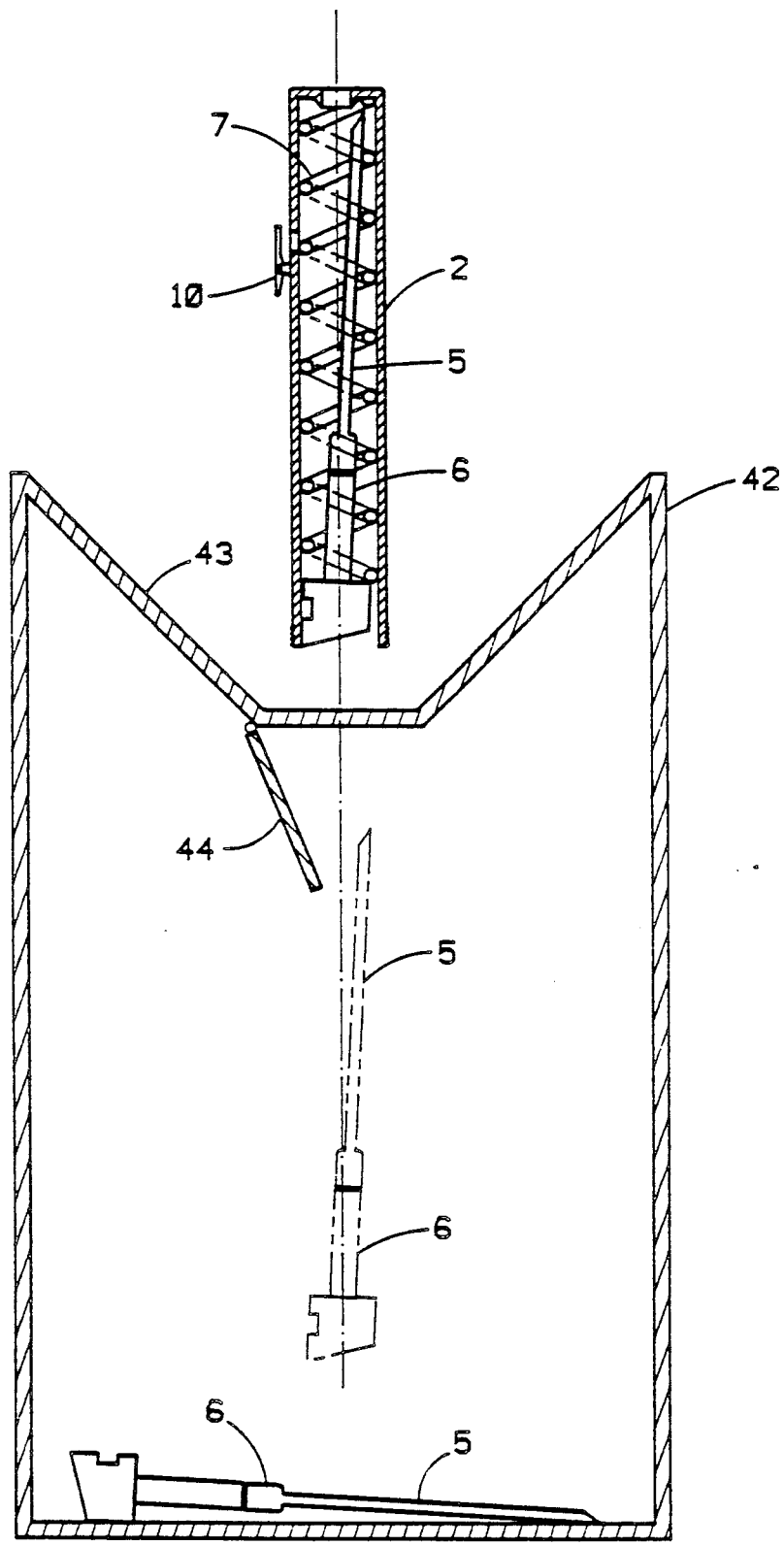

Referring to FIG. 7, there is shown a means of dumping the slidable piston 6 and the needle cannula 5 into a safety container 42.

The cap is removed from the elongated hollow barrel 2 and the elongated hollow barrel 2 is turned over. When the elongated hollow barrel 2 is turned over, the slidable piston 6 and the needle cannula 5 fall out into a safety container 42 with a funnel top 43 that will guide the slidable piston 6 and the needle cannula 5 into the safety container 42. At the bottom of the funnel top 43 is a safety door 44 that will close if the safety container is accidentally turned over, thus preventing the contaminated needle cannula 5 from falling out. When the slidable piston 6 and the needle cannula 5 are dumped into the safety container 42 they do not have to be touched and may be disposed of in the proper manner. The elongated hollow barrel 2, the latch means 10, and the spring 7, may be reused after they have been suitably sterilized.

Although the system described in detail supra has been found to be most satisfactory and preferred many variations are possible. For example, the blood sampling device may have two or more latch means, the blood sampling device could be square in section or the latch means could be placed closer to the needle cannula.

Although the invention has been described with reference to the preferred embodiment, it will be understood by those skilled in the art, that additions, modifications, substitutions, deletions, and other changes not specifically described, may be made in the embodiments herein, it should be understood that the details herein are to be interpreted as illustrative and are not in a limiting sense.

What is claimed as invention is:

1. A blood sampling device held by fingers and thumb for inserting a needle cannula into a body and drawing out blood or fluid from said body comprising:

an elongated hollow barrel having a first end and a second end and having an inner surface and an outer surface and further having a longitudinal axis in the center of the said elongated hollow barrel, parallel in most part of the said inner surface and said outer surface of the said elongated hollow barrel further extending from said first end to said second end of said elongated hollow barrel;

a barrel flange fixed to said first end of said elongated hollow barrel;

a slidable piston inside of said elongated hollow barrel, said slidable piston having a first end and a second end and said first end of said slidable piston is nearer said first end of said elongated hollow barrel;

a needle cannula having a first end a second end, said first end of said needle cannula extends past said first end of said elongated hollow barrel and said second end of said needle cannula is fixed to said first end of said slidable piston;

a spring means having a first end and a second end, said first end of said spring means is integral with said barrel flange of said elongated hollow barrel and said second end of spring means is integral with said slidable piston, said spring means is further compressed between said barrel flange of said elongated hollow barrel and said slidable piston;

at least one piston notch formed into said slidable piston said piston notch is near perpendicular to said longitudinal axis of said elongated hollow barrel;

a tunnel, said tunnel is formed inside of the slidable piston, said tunnel is fixed to the needle cannula to allow fluid or blood to flow through the needle cannula and into and through said tunnel formed in said slidable piston;

a needle cannula tunnel in said barrel flange;

at least one latch means for engaging with said slidable piston and said latch means further having a latch lever wherein said latch is disengaged from said slidable piston wherein said slidable piston is no longer restrained and said spring pushes said slidable piston and said needle cannula in the direction of the second end of said elongated hollow barrel until the said needle cannula is past the said barrel flange of the elongated hollow barrel, thus enclosing said needle cannula in said elongated hollow barrel and said barrel flange.

2. The blood sampling device of claim 1, wherein said slidable piston has a slope on the second end of said slidable piston.

3. The blood sampling device of claim 1, wherein said elongated hollow barrel has a cap on the second end, said cap to prevent said slidable piston from being removed unintentionally.

4. The blood sampling device of claim 1, wherein when said slidable piston and said needle cannula are retracted into said elongated hollow barrel, and wherein said slope at said second end of said slidable piston will push against the said second end of said elongated hollow barrel further causing said slidable piston and said needle cannula to slope inside of said elongated hollow barrel.

5. The blood sampling device of claim 3, wherein said cap may be removed and said elongated hollow barrel may be turned over and said needle cannula and said slidable piston may be dumped into a safety container.

6. The safety container of claim 5, wherein said safety container has a funnel located at the top of the said safety container, said funnel to guide any devices into said safety container.

* * * * *